United States Patent [19]

Kumar et al.

[11] Patent Number: 4,611,175
[45] Date of Patent: Sep. 9, 1986

[54] PIPE CORROSION MONITOR

[75] Inventors: Ashok Kumar, Champaign; Ellen G. Segan; John M. Bukowski, both of Urbana, all of Ill.

[73] Assignee: The United States of America as represented by the Secretary of the Army, Washington, D.C.

[21] Appl. No.: 592,140

[22] Filed: Mar. 22, 1984

[51] Int. Cl.⁴ .......................................... G01N 27/42
[52] U.S. Cl. .................. 324/425; 324/65 CR
[58] Field of Search ............. 324/456, 452, 425, 457, 324/71.2, 65 CR

[56] References Cited

U.S. PATENT DOCUMENTS

| 1,194,202 | 8/1916 | MacGahan | 324/113 |
| 2,860,304 | 11/1958 | Hall | 324/52 |
| 3,327,214 | 6/1967 | Allen et al. | 324/123 R |
| 3,337,798 | 8/1967 | Twining et al. | 324/65 CR |
| 3,406,101 | 10/1968 | Kilpatrick | 204/1 T |
| 3,684,679 | 8/1972 | Smith et al. | 204/404 |
| 3,792,350 | 2/1974 | Bossler et al. | 324/52 |
| 3,999,121 | 12/1976 | Taylor, Jr. | 324/65 CR |
| 4,019,133 | 4/1977 | Manley et al. | 324/65 CR |
| 4,051,436 | 9/1977 | Weir, Jr. | 324/102 |
| 4,080,565 | 3/1978 | Polak | 324/65 CR |
| 4,099,117 | 7/1978 | Erath et al. | 324/54 |
| 4,217,544 | 8/1980 | Schmidt | 324/65 CR |
| 4,262,247 | 4/1981 | Olson et al. | 220/268 |
| 4,356,444 | 10/1982 | Saenz | 324/425 |

Primary Examiner—Michael J. Tokar
Attorney, Agent, or Firm—Darrell E. Hollis

[57] ABSTRACT

Method and means for determining the corrosion status of a coated underground metallic object without the necessity of excavation. An electrical charge is produced on an area of the pipe, and the rate at which the charge decays is measured. The degree of corrosion of the object is measured as a function of the rate of decay of the charge and the area charged.

9 Claims, 2 Drawing Figures

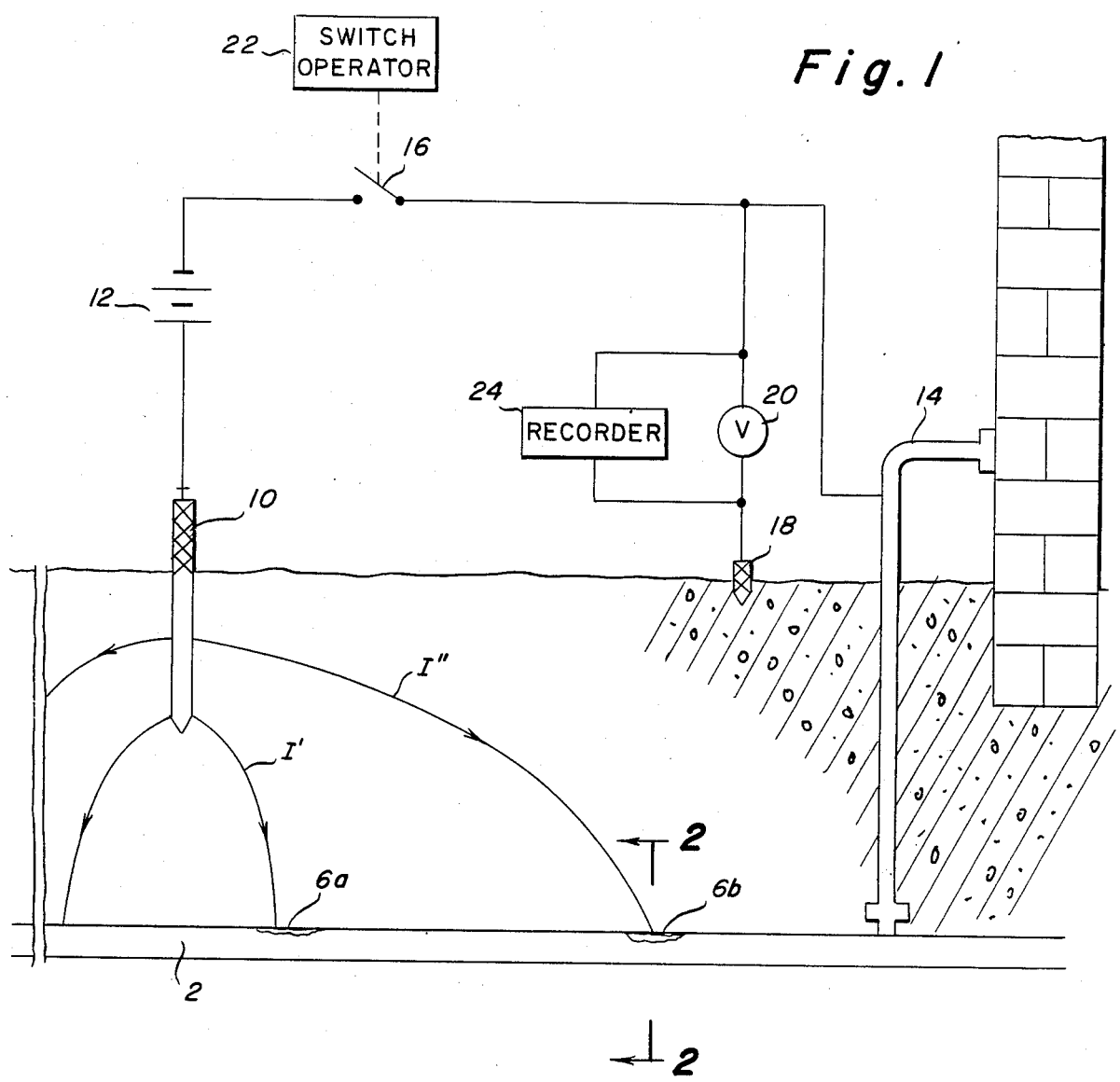
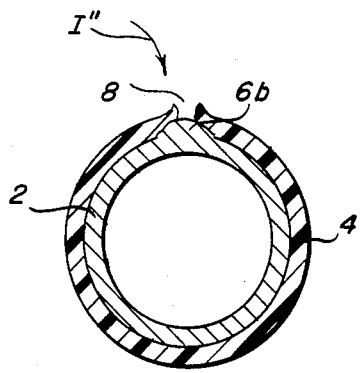

PIPE CORROSION MONITOR

STATEMENT OF GOVERNMENT INTEREST

The invention described and claimed herein may be manufactured and used by or for the Government of the United States of America for governmental purposes without the payment of royalties thereon or therefor.

BRIEF DESCRIPTION OF THE PRIOR ART

Metallic objects which have been buried in the soil corrode over a period of time at a rate which depends upon the soil corrosivity. In order to protect the object from corrosion, various coatings such as coal-tar enamels, mastics, waxes, polyethylene, polyvinyl chloride, and polypropylene have been coated onto the object before it is placed in the soil. These coatings are seldom perfect and degrade over a period of time. Corrosion products which form under the coating lift and crack the coating due to the volume expansion associated with the process of corrosion, thus allowing moisture present in the soil to seep under the coating and lead to further corrosion. As the object ages, the amount of exposed metal increases with the corrosion products accumulated under the debonded coating.

The corrosion status of coated underground pipe is needed in any life cycle cost analysis for making decisions about repairing projected leaks or replacement of new pipe. One method of determining the corrosion status of a coated underground pipe entails digging test holes (called bell holes) to allow visual inspection of the condition of the pipe. Digging bell holes, however, is both time consuming and difficult.

Another method uses an electrode placed in the ground to create a current path through the soil and to the underground object to cause a change in electrical potential on the object. The amount of applied current needed to cause a fixed potential change is proportional to the current caused by the corrosion process. Such systems possess certain inherent drawbacks, such as the difficulty in accurately measuring the magnitude of the current within a given period of time.

The present invention was developed to avoid the above and other drawbacks of the known corrosion measuring systems, and to provide an inexpensive system for accurately determining the effects of corrosion on a metal object.

SUMMARY OF THE INVENTION

According, a primary object of the present invention is to provide an improved method and apparatus for determining the corrosion status of a coated underground metallic object without the necessity of excavating the object.

A further object of the invention is to provide a method and apparatus for determining the corrosion status of a coated underground metallic object by measuring the rate at which an applied charge on the object dissipates.

These and other objects of the present invention are achieved by providing apparatus comprising an electrode inserted in the ground, a direct-current voltage source, circuit means connecting the voltage source between the electrode and the underground metallic object to establish a current path through the soil and to the object, thereby to charge the object to a certain level, and means for measuring the transient decay of the charge to provide an indication of the corrosion status of the object.

BRIEF DESCRIPTION OF THE DRAWING

Other objects and advantages of the invention will become apparent from a study of the following specification when viewed in the light of the accompanying drawing, in which:

FIG. 1 is a schematic diagram of the pipe corrosion monitoring apparatus and method of the present invention; and FIG. 2 is a sectional view taken along line 2—2 of FIG. 1.

DETAILED DESCRIPTION

Referring more particularly to the drawing, there is illustrated a coated underground metallic object, shown here as a pipe 2, having a non-conductive corrosion resistant protective layer 4 and areas of corrosion 6a and 6b. Layer 4 may be of any conventional material used to protect underground objects as, for example, coal-tar enamels, mastics, waxes, polyethylene, or other polymers suited for this purpose. As shown in FIG. 2, expansion due to corrosion on pipe 2 causes the layer 4 to lift and crack, thereby creating openings 8 in layer 4 which allow moisture from the soil to reach the pipe 2 and lead to further corrosion.

The extent of the degradation of the layer 4 may be ascertained by applying an electrical charge on the pipe 2 and measuring the rate at which the charge dissipates.

In order to charge the pipe 2, an electrode 10 is arranged in the soil and connected with one terminal of a direct-current voltage source 12. The other terminal of the direct-current voltage source is connected with the pipe 2. This connection is made by contacting a pipe riser 14 or, alternatively, by a probe bar contacting pipe 2. With switch 16 in a closed position electric current paths I' and II" pass from the electrode 10 to the corroded areas 6a and 6b of the pipe 2 through a current path in the soil and openings 8 in the layer 4 to thus provide a charge on the pipe 2.

The charge on the pipe 2 is monitored by measuring the difference of potential between the pipe 2 and reference cell 18 with a voltmeter 20. The reference cell 18 is preferably a copper/copper sulphate half cell commonly used in the art, but other reference voltage sources may be used equally as well.

One difficulty with measuring the charge on the pipe 2 with the reference cell 18 and voltmeter 20 is that the currents I', I" passing from the electrode 10 to the pipe 2 cause the voltmeter 20 to register the sum of two unknown voltages, namely, the charge on the pipe 2, and the voltage created by passage of the currents I', I" through the soil between the reference cell 18 and the pipe 2.

In order to avoid this difficulty, switch operator 22 periodically opens switch 16 to interrupt the currents I', I". The voltmeter 20 is tuned with the switch operator 22 so that measurements are taken only when switch 16 is open and the currents I', I" are interrupted. Preferably, switch operator 22 opens switch 16 sixty times per second. The currents I', I", therefore, are applied in discrete increments, each increment shifting the charge on pipe 2, and the charge on the pipe is measured during the off-current periods.

The charge on the pipe 2 is shifted in the negative direction to −850 millivolts with respect to the reference cell 18 by the current increments. The off-current charge on the pipe 2 is maintained at −850 millivolts with respect to the reference cell 18 for approximately one hour, and the switch operator 22 then causes the switch 16 to stay in an open position, thus preventing further current flow.

Once the current flow is interrupted, the charge on the pipe 2 will rapidly decay. The rate of decay of the charge may be recorded by a recorder 24 connected between the reference cell 18 and the pipe 2. The rate at which the charge decays is a function of the degree of corrosion of the pipe 2 and the area of the pipe which is electrically continuous. The area of the pipe charged can be determined by making potential measurements by placing a reference cell on the ground on top of the pipe and connecting it with one lead of a potential measuring device having its other lead connected to the pipe riser.

After the current is shut off, the charge on the charged portion of pipe 2 is allowed to decay an amount $\Delta V$, usually 100 millivolts, in the time period $\Delta t$. The relaxation rate R is defined as $\Delta V/\Delta t$ per unit area of pipe charged. The relaxation rate R is correlated to the degree of corrosion of the charged section of the pipe by the equation:

$$R = AF^{0.4}$$

where A is a constant and F is the ratio of the corroded area of the charged section of the pipe to the total area of the charged section of the pipe. This ratio F is an indication of the corrosion status of the pipe 2.

What is claimed is:

1. The method for measuring the amount of corrosion occuring since placement of a metalic object which is coated with a non-conductive, corrosion-resistant protective layer, said object being buried in situ in the soil, which comprises the steps of:
   (a) introducing an electrode into the soil adjacent said object;
   (b) applying a direct-current potential between said electrode and said object, thereby establishing a current path from said electrode to the object via the soil and at least one opening produced in the protective layer of the corrosion of a given area of said object, thereby electrically charging the object to a given level relative to electrical ground;
   (c) opening the current path after the charge on said object reaches said given level; and measuring the transient decay of the charge, thereby providing an indication of the amount of corrosion of the object occuring since placement.

2. The method as defined in claim 1, wherein the step of measuring the transient decay of the charge comprises:
   (a) introducing into the soil a reference cell operable to produce a given reference voltage; and
   (b) connecting a measuring device between said reference cell and said object.

3. The method as defined in claim 2, wherein said reference cell is a copper/copper sulphate half cell.

4. The method defined in claim 2, and further including the preliminary steps of
   (a) periodically interrupting said current to produce off-current periods; and
   (b) determining by means of said measuring device when said object is charged to said given level.

5. Apparatus for measuring the amount of corrosion occuring since placement of a metallic object coated with a non-conductive, corrosion-resistant protective layer, said object being buried in situ in the soil, comprising:
   (a) an electrode adapted for insertion onto the soil adjacent said object;
   (b) a direct-current voltage source;
   (c) circuit means connecting said voltage source with said electrode and said object to establish a current path from said electrode to the object via the soil and at least one opening produced in the protective layer by the corrosion of a given area of the object, thereby electrically charging the object to a given level relative to electrical ground;
   (d) means for opening said circuit path after the charge in said object reaches a given level; and
   (e) means for measuring the transient decay of the charge, thereby providing an induction of the amount of corrosion of the object occurring since placement.

6. Apparatus defined in claim 5, wherein said decay measuring means includes:
   (1) a reference cell inserted in the soil and operable to produce a given reference voltage; and
   (2) a measuring device connected between said reference cell and said object.

7. Apparatus defined in claim 6, wherein said reference cell is a copper/copper sulphate half cell.

8. Apparatus defined in claim 6, wherein said measuring device includes:
   (a) a voltmeter for measuring the charge on said object; and
   (b) a chart recorder for recording the charge on said object as a function of tune.

9. Apparatus defined in claim 6, and further including means for periodically interrupting said current to produce off-current periods during which the charge on the object is measured by said measuring device to determine when the charge reaches said given level.

* * * * *